United States Patent [19]
Bab et al.

[11] Patent Number: 5,755,572
[45] Date of Patent: *May 26, 1998

[54] ORAL HYGIENE IRRIGATOR SYRINGE BULB

[75] Inventors: Itai Bab, Karmel Yossef; Gadi Porat, Jerusalem, both of Israel

[73] Assignee: Novadent Ltd., Jerusalem, Israel

[*] Notice: The term of this patent shall not extend beyond the expiration date of Pat. No. 5,558,518.

[21] Appl. No.: 705,618

[22] Filed: Aug. 30, 1996

Related U.S. Application Data

[63] Continuation-in-part of Ser. No. 104,998, Aug. 10, 1993, Pat. No. 5,558,518.

[30] Foreign Application Priority Data

Aug. 10, 1992 [IL] Israel .......................... 102776

[51] Int. Cl.$^6$ .................................. A61G 17/02
[52] U.S. Cl. ............................ 433/80; 433/216
[58] Field of Search .................. 433/80, 216, 88, 433/89, 215; 604/204, 212, 216; 601/162, 141; 222/211, 212, 463, 464

[56] References Cited

U.S. PATENT DOCUMENTS

| | | | |
|---|---|---|---|
| 807,905 | 12/1905 | Blair | 604/212 |
| 1,166,033 | 12/1915 | Yoder | 433/89 X |
| 2,978,152 | 4/1961 | Batty | 222/394 |
| 3,088,680 | 5/1963 | Fulton et al. | 239/327 |
| 3,199,510 | 8/1965 | Sinai | 604/212 X |
| 3,211,349 | 10/1965 | Prussin et al. | 222/394 |
| 3,480,009 | 11/1969 | Sinai . | |
| 3,490,656 | 1/1970 | Taschner | 222/464 |
| 3,667,655 | 6/1972 | Knieriem, Jr. | 222/464 |
| 3,809,977 | 5/1974 | Balamuth et al. | 433/119 X |
| 4,062,475 | 12/1977 | Harris et al. | 222/95 |
| 4,069,950 | 1/1978 | Archer | 222/211 X |
| 4,177,939 | 12/1979 | Tomas | 222/183 X |
| 4,286,735 | 9/1981 | Sneider | 222/464 X |
| 4,512,769 | 4/1985 | Kozam et al. | 433/80 |
| 4,787,845 | 11/1988 | Valentine | 433/80 |
| 4,828,546 | 5/1989 | McNeil et al. | 604/73 |
| 4,830,235 | 5/1989 | Miller | 222/464 |
| 4,958,751 | 9/1990 | Curtis et al. | 433/80 |
| 4,973,250 | 11/1990 | Milman | 433/80 |
| 4,993,941 | 2/1991 | Maita et al. | 433/80 |
| 5,125,543 | 6/1992 | Rohrabacher et al. . | |
| 5,127,831 | 7/1992 | Bab . | |
| 5,137,183 | 8/1992 | Mikulec et al. | 222/192 |
| 5,195,664 | 3/1993 | Rhea | 222/464 |

FOREIGN PATENT DOCUMENTS

| | | |
|---|---|---|
| 1479528 | 5/1967 | France . |
| 1565071 | 4/1969 | France . |
| 2101505 | 3/1972 | France . |
| 2222841 | 10/1974 | France . |
| 2437246 | 4/1980 | France . |
| 3936409 | 5/1991 | Germany . |
| 902114 | 7/1962 | United Kingdom . |
| 1008733 | 11/1965 | United Kingdom . |
| 2136057 | 9/1984 | United Kingdom . |
| 2217394 | 10/1989 | United Kingdom . |
| 2234555 | 2/1991 | United Kingdom . |
| 2237743 | 5/1991 | United Kingdom . |

*Primary Examiner*—Nicholas D. Lucchesi
*Attorney, Agent, or Firm*—Frommer Lawrence & Haug LLP; William S. Frommer

[57] ABSTRACT

An oral irrigator syringe bulb having an elastic compressible bulb, which may be filled with irrigation fluid, and a rigid nozzle having a base portion which may be sealingly fitted to the bulb. The nozzle has a lumen along the longitudinal axis thereof, and the lumen has a fluid outlet at its upper part to which suitable irrigation means can be attached. The nozzle also has an elongate non-kinking flexible dip tube which reaches into the lumen, the free end of the dip tube being provided with a weight, whereby when the nozzle is fitted onto the bulb the free end of the dip tube extends into the bulb and is submerged in the irrigation fluid at any spatial position in which the bulb is held.

29 Claims, 4 Drawing Sheets

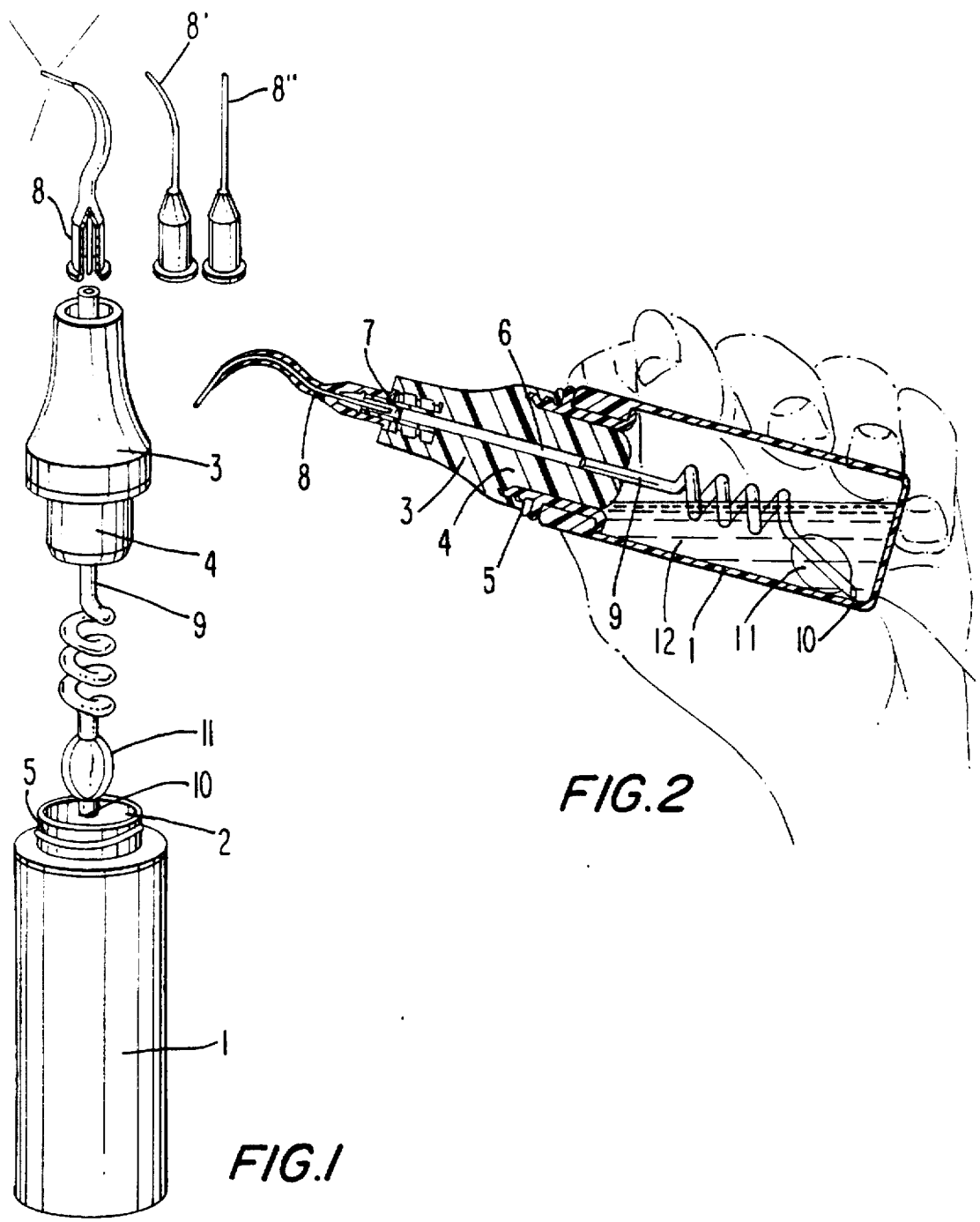

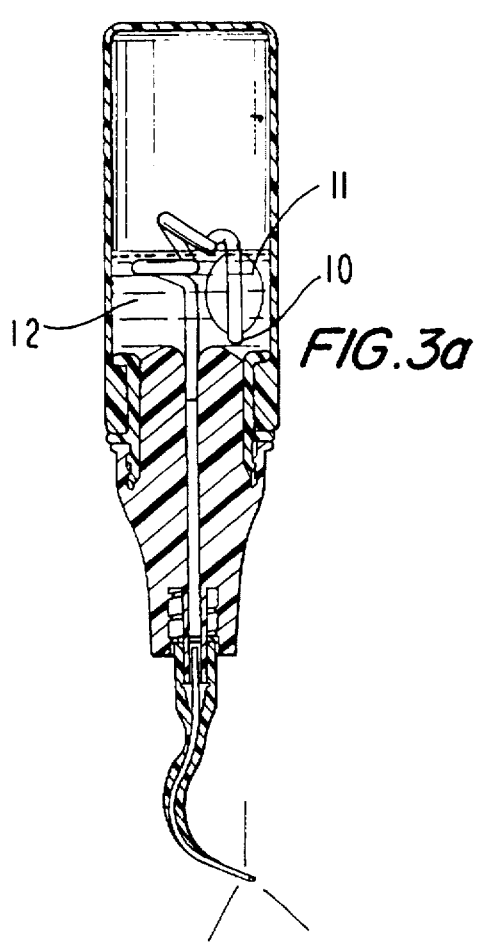
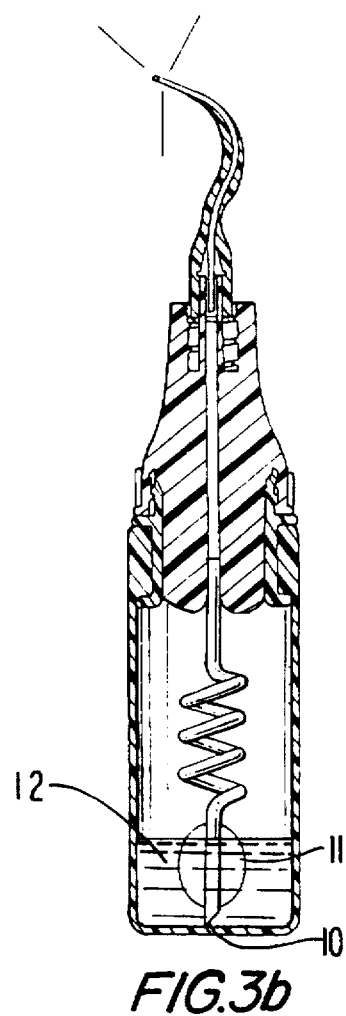
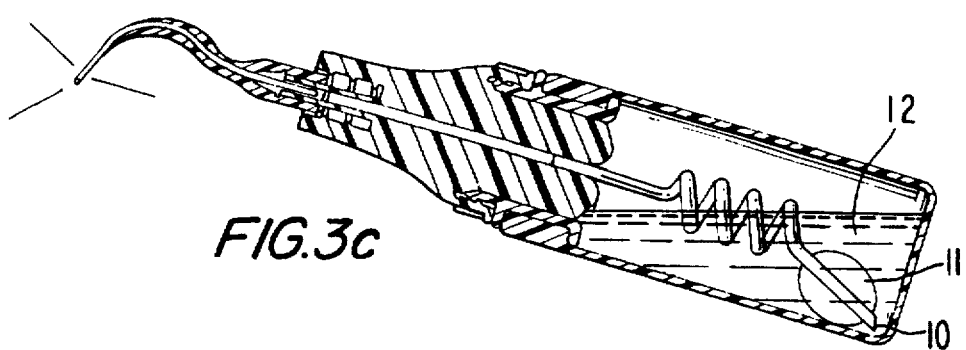
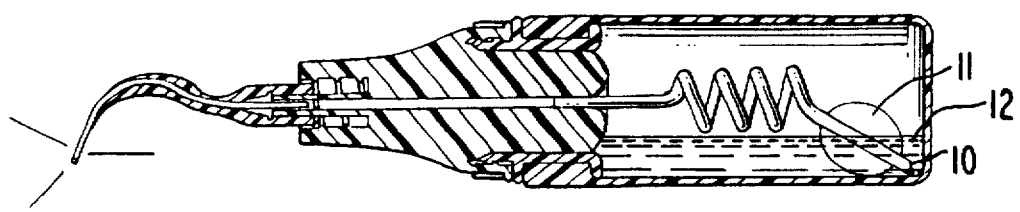

ORAL HYGIENE IRRIGATOR SYRINGE BULB

This application is a continuation-in-part of U.S. application Ser. No. 08/104,998, filed on 10 Aug. 1993 now U.S. Pat. No. 5,558,518.

FIELD OF THE INVENTION

The present application relates to an oral irrigation fluid dispensing device, which may be equipped with a suitable irrigation device, for the delivery of medically compatible fluids into the periodontal pocket or the gingival sulcus of the interdental space. The present application further relates to such a device specifically equipped with an irrigating brush accessory for brushing and irrigating the external surfaces of the teeth and the gingival sulcus.

BACKGROUND OF THE INVENTION

Periodontal inflammation is one of the most common diseases of the adult population. Periodontal inflammation is induced by the dental plaque, a mixture of bacteria embedded in an adhesive matrix, present on the tooth surface particularly at the interdental spaces and near the gums. The initial pathological reaction to the plaque, called gingivitis, is expressed by the soft gum tissue as redness, bleeding, swelling, bad breath and sour taste. Later, over a period of several years, the gum disease progresses and causes destruction of the tooth supporting bone, leaving a pathologic space between the tooth root and the gum. This space is the periodontal pocket. The plaque extends into the pockets, from which it cannot be removed by conventional oral hygiene methods, such as brushing and flossing. This plaque induces further damage, increasing the pocket size in depth and width, with eventual tooth loss. In addition to the gingivitis, plaque present in the interdental space also causes interproximal tooth decay.

Since the implication of plaque in the development of dental diseases, the majority of plaque control devices introduced over the past decades have been developed for supragingival plaque removal. Supragingival plaque can be effectively removed by brushing and flossing, but most brushing and flossing devices are restricted by physical restraints that limit their ability to extend far enough below the gingival margin. The configuration of tooth picks, pipe cleaners, interdental brushes and other interdental cleaning aids also limits the effect of these devices on subgingival plaque. Furthermore, antiplaque agents used as mouth rinses affect only supragingival plaque unless agents are introduced below the gingival margin with an irrigating device. Oral irrigators allow practitioners and patients access to subgingival areas in order to disrupt the plaque that proliferates at these sites.

Irrigation can be defined simply as "the flushing of a specific site or area with a stream of fluid delivered by an irrigator". In 1968, the first powered oral irrigation device, WaterPik® (Teledyne WaterPik), was accepted by the American Dental Association for its ability to remove food particles and debris from interdental areas and below the gum line. This device was widely recommended, particularly for orthodontic and prosthodontic patients. However, research was unable to establish a definite relationship between the presence of debris and periodontal disease and found no evidence that irrigation with WaterPik® could significantly reduce plaque. Subsequent research utilizing antimicrobial solutions delivered by an oral irrigator equipped with a fine probe, has helped to establish oral irrigation as a useful procedure for plaque control, especially for "site specific" therapeutic approaches that require direct delivery of antimicrobial solutions into the affected sulcus or pocket, and has expanded the usefulness of the irrigator in preventative care, beyond its application as a mechanism to simply flush away debris.

Researchers of general preventive techniques, dental hygiene educators as well as various practitioners, have maintained that oral irrigation is an effective adjunctive plaque control therapy throughout the course of periodontal treatment, from initial plaque removal instruction through maintenance. Furthermore, experts gathered at the April 1991 meeting of the International Association of Dental Research in Acapulco, Mexico, agreed that the use of antimicrobial solutions applied with oral irrigation systems exhibits high promise in the site specific treatment of periodontal conditions.

Irrigators designed for home care by the patient consist of a power driven pump or flexible syringe bulb and a tip. The early irrigator tips, designed for supragingival removal of debris were too large to penetrate the interdental space and gingival sulcus of patients with undisrupted gum architecture or periodontal pockets. In addition, the motor driven pumps deliver a powerful stream that causes undesirable enforcement of debris and microorganisms into the dental tissues. Subgingival irrigation devices, introduced into the dental market over the past decade, are capable of delivering medicaments directly to the site of the periodontal infection. This form of therapy can effectively remove bacterial plaque in sites inaccessible to brushing, flossing and other mechanical manipulations [a variety of available irrigation devices can be found in Dental Products Report® Europe (also published in the U.S.A.), MEDEC Dental Communications, A Division of Medical Economics Publishing Company, Inc., October 1991].

However, one of the main drawbacks of oral hygiene techniques used for arrest or prevention of periodontal diseases, particularly irrigation, is patient compliance, since the patient should maintain routine, day-by-day treatment. A great deal of the non-compliance can be attributed to the non-handiness of most available oral irrigators.

U.S. Pat. No. 5,127,831, corresponding to co-pending Israel Patent Application. No. 98355, discloses a novel irrigation probe, particularly suitable for use by a patient. Conventional irrigation devices, like blunt, rigid metal needless, are also used for irrigation, by trained personnel [e.g. Soh, L. L., et al. J. Clin. Periodontal. 9: 66–74 (1982), J. G. L. Khoo and H. N. Newman, J. Periodont. Res. 18: 607–619 (1983)]. Another dental irrigation needle is disclosed in U.S. Pat. No. 4,993,941. Additionally, IMAX® Periotips® (SDI Group, Inc., IL U.S.A.) are used for in-office professional subgingival irrigation.

All of the known prior art irrigation probes can be used with various pumping devices containing the irrigation fluid, which may be water or medically compatible solutions. These devices include different manual and automatic syringes, spray injectors and mechanically or electrically driven pump systems. The known pumping devices, particularly syringes, are mostly designed for in-office use by trained personnel.

Another pumping device, stated to be suitable for use by a patient, is sold under the name Luer Syrette® (Perio Dental, Inc., Colorado USA). This pumping device consists of a compressible bulb, which has a narrow opening, and a hollow shaft. One end of the shaft can be sealingly fitted into the opening in the bulb, the other end has a luer lock for connecting the irrigation probe. This Luer Syrette® is only operable when held in an upright position. Thus, in order to irrigate lower jaw sites, or other sites which are difficult to reach, an elongate extension tube is used, connecting said luer lock with the irrigation probe, to enable the attending dentist or the patient to reach all subgingival pockets, while maintaining the Luer Syrette® in the upright position. To achieve the upright position, both hands of the user are engaged which is a drawback since one hand should preferably be free, to push aside the lip/s or cheek/s to expose the target site. In addition, the structure of the Luer Syrette® is rather complex, since it requires the inclusion of an anti-suction valve, preventing suction of the irrigation fluid back into the bulb when pressure on the bulb is released. Moreover, the bulb opening is narrow and the bulb is filled with the irrigation fluid by suction from a larger container. Also washing of the bulb with water between uses is achieved by suction. Evidently, the fact that the bulb can only be operated when in an upright position is a major drawback, particularly when considering the anatomy of the mouth, and especially when used by the patient.

The present invention intends to overcome the described drawbacks, essentially by providing an irrigation device which is equipped with a non-kinking weighted dip tube, which is submerged in the irrigation fluid irrespective of the spatial position in which the irrigator is held.

Various fluid dispensing devices comprising a weighted dip tube assembly, some of them non-kinking tubes, which ensures that the free end of the dip tube is always submerged in the fluid to be dispenses are known. Such fluid dispensing devices are described, for example, in UK Patent Applications Nos. 902,114, 1,008,733, 2,136,057, 2,217,394 and 2,234,555, U.S. Pat. Nos. 2,978,152, 3,088,680, 3,211,349, 3,490,656 and 3,667,655, DE 36 36 409 and French Patent Applications Nos. 1,479,528, 1,565,071, 2,101,505 and 2,437,246. However, none of the dispensers disclosed in these publications is intended for dental use and in all of the disclosed dispensers, the container is rigid and the pressurized fluid is dispensed by aerosol means. Moreover, the prior art dispensers appear to be only suitable for one-time use and cannot be refilled.

Another aim of the present invention is to provide a device, and corresponding method, for brushing and irrigating the external surfaces of the teeth and the gingival sulcus, said device being equipped with a non-kinking weighted dip tube, which is submerged in the irrigation fluid irrespective of the spatial position in which the irrigator is held, and further comprising a brush attachment having at least one fluid outlet in proximity to the bristles, said outlet being in communication with the irrigation fluid inside the device.

BRIEF DESCRIPTION OF THE INVENTION

The present invention relates to an oral irrigator syringe bulb comprising an elastic compressible bulb, which may be filled with the irrigation fluid, having an opening, and a rigid nozzle having a base portion which may be sealingly fitted to said bulb opening, and a lumen along the longitudinal axis thereof, the lumen having a fluid outlet at the upper-part thereof, to which suitable irrigation means can be attached, and an elongate non-kinking flexible dip tube accommodated therein, one end of said dip tube reaching into said lumen, the free end of the said dip tube being provided with a weight whereby when the nozzle is fitted onto the bulb the free end of said dip tube extends into the bulb and is submerged in the irrigation fluid at any spatial position in which the bulb is held.

BRIEF DESCRIPTION OF THE FIGURES

FIG. 1 illustrates an exploded view of an oral irrigator syringe bulb according to an embodiment of the present invention;

FIG. 2 illustrates a longitudinal cross-sectional view of the oral irrigator illustrated in FIG. 1;

FIGS. 3A–3D illustrate longitudinal cross-sectional views of the oral irrigator illustrated in FIG. 1, in upside-down, upright inclined and horizontal positions, respectively.

DETAILED DESCRIPTION OF THE INVENTION

Figure 4A:
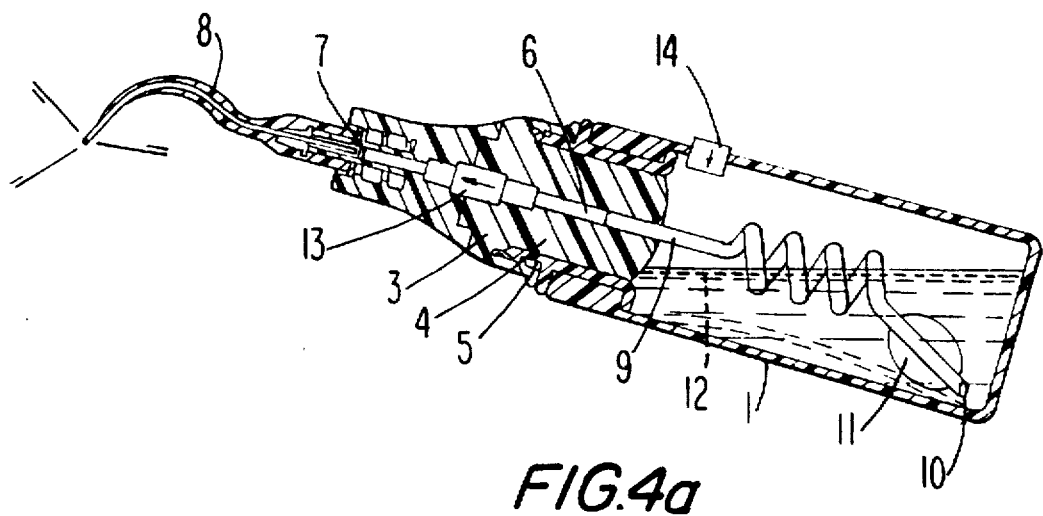
FIGS. 4A–4B illustrate a longitudinal cross-sectional view of an oral irrigator syringe bulb according to another embodiment of the present invention.

The present invention relates to an oral irrigator syringe bulb comprising essentially two parts: (i) an elastic compressible bulb, which may be filled with the irrigation fluid, the bulb having an opening; and (ii) a nozzle having a base portion, which may be sealingly fitted to said bulb opening, and a lumen along the longitudinal axis thereof, having a fluid outlet at one end thereof, to which suitable irrigation means, such as probes, tips, needles or irrigating brush accessories, as hereinafter described, can be attached, and an elongate non-kinking flexible tube accommodated within said nozzle, one end of said dip tube reaching into the said lumen, the free end of said dip tube being provided with a weight. Thus, when the nozzle is fitted onto the bulb, the free end of said dip tube extends into the bulb and, due to the weight attached thereto, is submerged in the irrigation fluid at any spatial position in which the bulb is held. Upon compression of bulb, the irrigation fluid is urged into the lumen through said dip tube and from the lumen into the irrigation tip through said fluid outlet.

The bulb may be essentially ball- or pear-shaped or essentially cylindrical. The bulb may be made from any suitable elastic material, for example, rubber, silicon rubber and soft polyvinylchloride, which are medically compatible materials, are preferred. The opening of the bulb may be provided with means for sealingly fitting the base portion of the nozzle thereto. These means may be threads, o-rings, bayonets or any other suitable means providing for sealed-fitting.

The bulb opening can be large enough to enable filling the bulb with the irrigation fluid by simply pouting the irrigation fluid thereinto, optionally via a funnel, before fitting the nozzle thereon. The bulb can be washed, between uses, in the same manner, after removing the nozzle. This facilitates use considerably.

The nozzle may be made from any suitable rigid material, preferably rigid medically compatible plastic material. The base portion of the nozzle, which is to be sealingly fitted to the bulb opening, may be provided with means for said sealed-fitting, which correspond to the sealing means provided on said opening, and which may be threads, o-rings, bayonets or any other suitable means providing for sealed-fitting. The nozzle may be manufactured in the form of a single, integral part, or it can be mounted from separate parts.

The non-kinking dip-tube can be straight or spiral, and can be made from any suitable medically compatible material. Preferred materials are polyvinylchloride and other soft plastic materials, rubber, silicon-rubber and latex.

The irrigation means, for example tips, probes, needles or irrigating brush accessories, as hereinafter described, are attached to the irrigator via the fluid outlet, which is suitably designed or can optionally be equipped with means for attaching the irrigation means, such means being known in the art.

Said irrigating brush accessories may thus comprise a brush stem having at one end said means for attaching the irrigating brush accessory to the irrigator, and comprising at the other end of the brush stem a plurality of suitable bristles for brushing the external surfaces of the teeth and the gingival sulcus. Such bristles, and their arrangement on the stem of a brush, are well known in the art. The stem further comprises at least one channel means which communicates with the fluid outlet of the irrigator, when attached thereto, and to at least one fluid outlet suitable located preferably in the vicinity of the said bristles. Preferably, said channel means comprises a lumen within the brush stem, though alternatively a suitable pipe arrangement may be used.

The weight which is attached to the free end of the dip tube is made from a suitable material having a high specific gravity, preferably metal.

The present invention also relates to a method of treating or preventing periodontal disease or of improving dental hygiene. The irrigator of the present invention may be equipped with a suitable irrigation tip or probe, for irrigating interdental spaces and pathologic spaces formed between the soft gum tissue and the tooth root with water or a suitable medically compatible solution. Alternatively, the irrigator fluid dispensing apparatus according to the present invention may be equipped with an irrigating brush accessory for brushing and irrigating the external surfaces of the teeth and the gingival sulcus with water or said medically compatible solution. For example, antiseptic/antibiotic solutions can be used.

A preferred embodiment of an oral irrigator fluid dispensing apparatus according to the invention is illustrated in the appended Figures. As may be seen in FIGS. 1 and 2, the oral irrigator comprises a bulb (1), which has an opening (2). The second part of the oral irrigator is a nozzle (3). The nozzle has a base portion (4), which may be sealingly fitted to the bulb opening (2). In the illustrated embodiment, the sealed fitting is achieved by means of threads. The nozzle (3) is threaded onto the bulb at opening (2) by means of threads (5) and corresponding threads on the base portion (4) of the nozzle. The threads can be replaced by other sealing means known to the man skilled in the art, such as o-rings, bayonets and the like. The bulb opening and the base part of the nozzle can also be so dimensioned as to achieve sealed-fitting by pressure only, pressing the base portion of the nozzle into the bulb opening, without the need for any particular sealing means.

The nozzle (3) has a lumen (6), along the longitudinal axis thereof, ending wit a fluid outlet (7) at the upper end thereof. This fluid outlet is designed to be fitted with any suitable irrigation tips, probes or needles (8, 8', 8"), or an irrigating brush accessory (20), as hereinafter described. Alternatively the fluid outlet (7) may be equipped with means known in the art for attaching the irrigation means thereto.

The nozzle (3) is further provided with an elongate, flexible non-kinking dip tube (9). The illustrated dip tube is spiral, but it can also be non-spiral. One end of the dip tube (9) is accommodated within said lumen (6), the free end of said dip tube (10) is provided with a weight (11). As may be seen in FIGS. 3A to 3D, the weight (11) ensures that the free end (10) of the dip tube to which it is attached is submerged in irrigation fluid (12) at any spatial position in which the oral irrigator is held (upside-down—FIG. 3A; upright—FIG. 3B; inclined—FIG. 3C; horizontal—FIG. 3D). Upon compression of the bulb (1), the irrigation fluid (12) is urged via the dip tube, through the opening at said free end thereof (10), into the said lumen (6), and from there into the irrigation tip (8), through said fluid outlet (7).

Figure 4B:
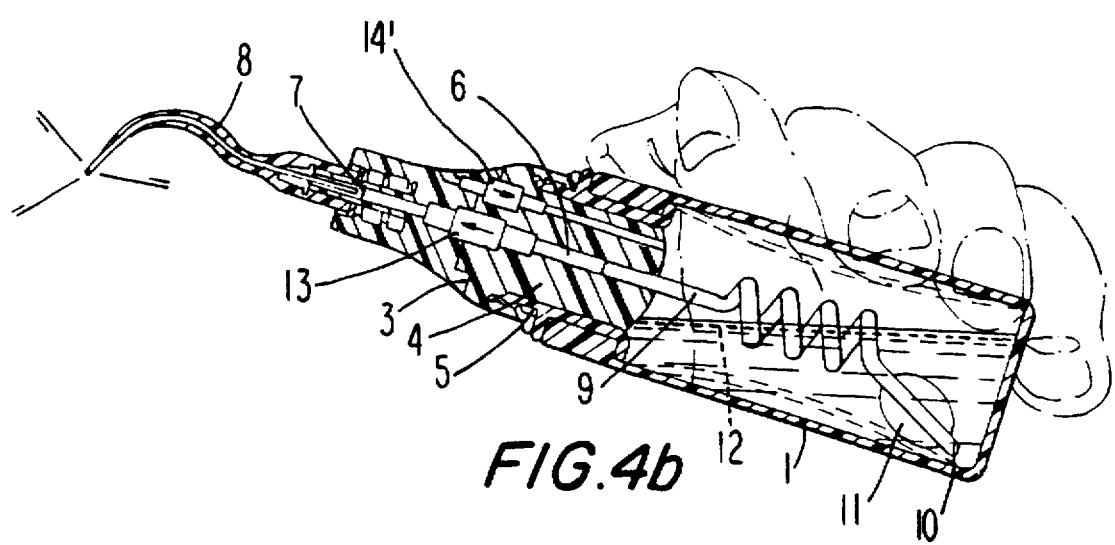

FIGS. 4A and 4B illustrate another embodiment of the present invention in which the syringe of FIG. 1 is equipped with one-way valves. In this embodiment, the nozzle may be equipped with a one-way valve, which may be located within the lumen of the nozzle, which permits exit of the irrigation fluid through the nozzle and the irrigation means into the oral cavity, but prevents back-flow or oral fluids, e.g. saliva back into the bulb. In this embodiment, contamination of the bulb and of the irrigation fluid contained therein by contaminants such as oral bacteria or blood is prevented, improving hygiene. Alternatively, this one-way valve may be located in other portions of the oral irrigator, such as within the dip tube (9) or the irrigation means (8). In this embodiment, a second one-way valve may be provided, to permit suction of air into the bulb. This second one-way valve prevents the irrigation fluid from escaping therethrough and may be situated at any convenient location, for example, at any outside wall of the bulb, or on the rigid nozzle.

As illustrated in FIGS. 4A and 4B, the nozzle (3) may be further equipped with a one-way valve (13), accommodated within the lumen (6). The one-way valve (13) allows for exit of the irrigation fluid (12) to the irrigation means (8), but prevents back-flow of any oral fluids into the bulb (1) and irrigation fluid (12). A second one-way valve (14 in FIG. 4A; 14 in FIG. 4B) permits suction of air into the bulb. As is to be appreciated, elements similar to those in FIGS. 1–3 are identified by the same reference numerals, and accordingly a further description is omitted herein.

Figure 5:
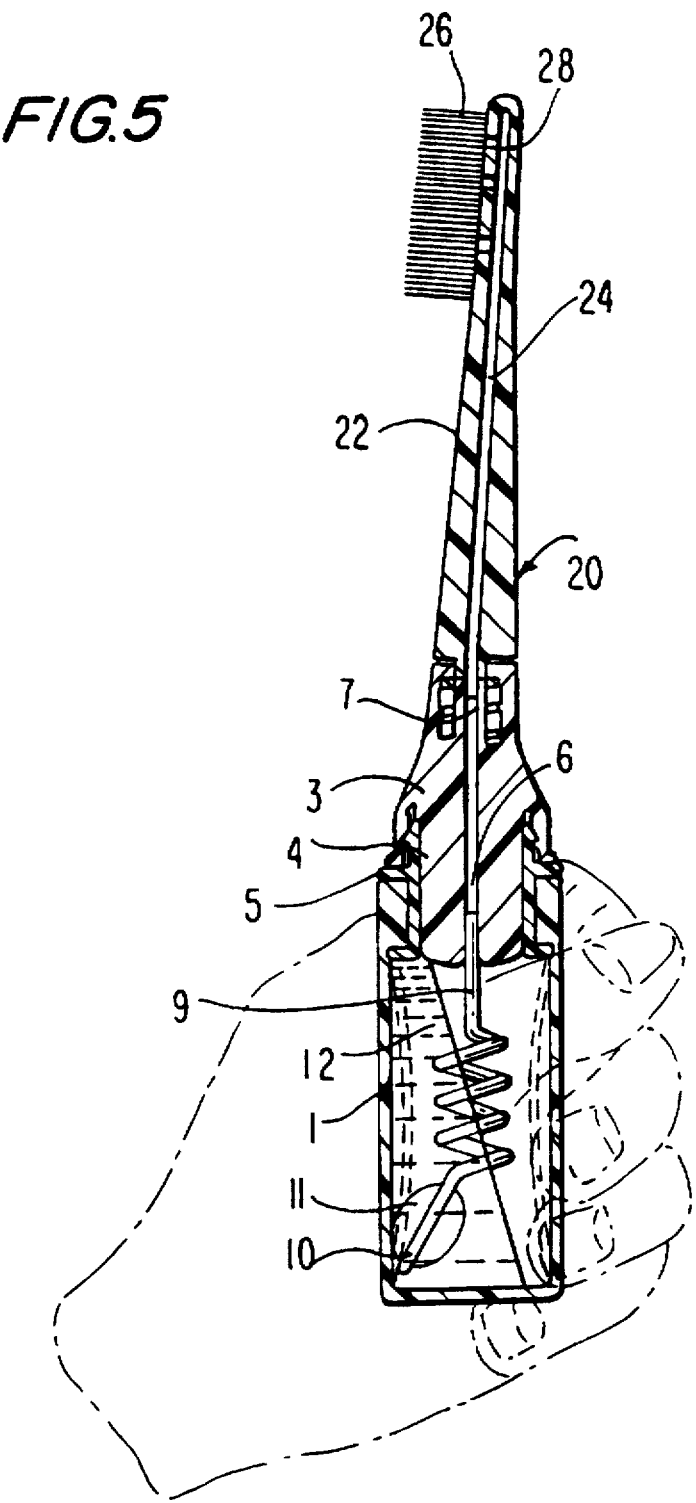
FIG. 5 illustrates a longitudinal cross-sectional view of an oral irrigator syringe bulb according to another embodiment of the invention comprising an irrigating brush accessory.

A preferred embodiment of the said irrigating brush accessory (20) is illustrated in FIG. 5, shown fitted to the fluid outlet (7) of the oral irrigator. The said irrigating brush accessory (20) comprises a brush stem (22) having at one end suitable means for attaching the said irrigating brush accessory (20) to the oral irrigator, and comprising at the other end a plurality of suitable bristles (26) for brushing the external surfaces of the teeth and the gingival sulcus.

The stem (22) further comprises at least one channel means which communicates with the fluid outlet (7) of the oral irrigator, when attached thereto, and to at least one brush fluid outlet (28) preferably located in the vicinity of the bristles (26). In the preferred embodiment, the said channel means comprises a lumen (24) along the longitudinal axis of the stem (22), said axis being preferably co-axial with the longitudinal axis of the nozzle lumen (6) at least in the vicinity of the said outlet (7). Alternatively, said channel means may comprise a tube or pipe communicating between said fluid outlet (7) and said brush fluid outlet (28). In the preferred embodiment, the stem (22) comprises a rectilinear longitudinal axis, though alternatively this axis may comprise at least one kink and/or may be curved. Such bristles (26), and their arrangement on the stem (22) are well known in the art.

This embodiment may be used to brush the external surfaces of the teeth and the gingival sulcus in the normal manner, at the same time irrigating same with the irrigation fluid (12).

While several embodiments have been described in detail the invention is not limited thereto, and many modifications and variations may be effected by one skilled in the art without departing from the spirit and scope of the invention as defined by the appended claims.

What is claimed is:

1. A method of treating or preventing periodontal disease and/or of improving oral hygiene, said method comprising the steps of:

filling an elastic compressible bulb of an oral irrigator fluid dispensing apparatus with an irrigation fluid wherein the irrigation fluid always settles to a low region within an internal cavity of the bulb in any spatial orientation of the bulb;

attaching said bulb to a base portion of a nozzle of said apparatus, said nozzle including a lumen having a fluid outlet at an upper portion thereof and a flexible, non-kinking tube, one end of said tube being coupled to a lower portion of said lumen and another fluid inlet end being attached to a weight and extending into said cavity of said bulb to provide for means for constantly maintaining said fluid inlet end of said tube in the irrigation fluid regardless of the spatial orientation of the bulb, with the tube being of a sufficient length and flexibility such that with the cooperation of the weight, the fluid inlet end of the tube is contained in said low region so as to enable the irrigation fluid to flow through the flexible tube to the nozzle regardless of a spatial orientation of said bulb;

attaching a desired irrigating brush accessory to the fluid outlet of said lumen, said irrigating brush accessory having a stem comprising suitable bristles at a first end thereof and suitable channel means communicating between at least one brush fluid outlet located at or near said first end, and said lumen of said oral irrigator when said irrigating brush accessory is attached thereto; and irrigating the external tooth surfaces by compressing said bulb of said apparatus so as to cause said irrigation fluid to flow through said tube and said lumen and into the said irrigating brush accessory, whereupon said irrigation fluid is dispensed to the tooth surfaces; and brushing the tooth surfaces in the normal manner with said irrigating blush accessory either together with or interspaced with the irrigation of same.

2. An oral irrigator fluid dispensing apparatus comprising:

an elastic compressible bulb having an opening and an internal cavity for holding an irrigation fluid therein and wherein the irrigation fluid always settles to a low region of the internal cavity within the bulb in any spatial orientation of the bulb;

a weight;

a rigid nozzle having a base portion to which the bulb opening is attached, a lumen having a fluid outlet at an upper portion thereof, and a flexible, non-kinking tube, one end of said tube being coupled to a lower portion of said lumen and another fluid inlet end being attached to said weight and extending into said cavity of said bulb to provide for means for constantly maintaining said fluid inlet end of said tube in the irrigation fluid regardless of the spatial orientation of the bulb, with the tube being of a sufficient length and flexibility such that with the cooperation of the weight, the fluid inlet end of the tube is contained in said low area so as to enable the irrigation fluid to flow through the flexible tube to the nozzle regardless of the spatial orientation of said bulb;

irrigation means coupled to said fluid outlet of said lumen for dispensing said irrigation fluid therefrom by compressing said bulb and including an irrigating brush accessory having a stem comprising suitable bristles at a first end thereof and suitable channel means communicating between at least one brush fluid outlet located at or near said first end, and said lumen of said oral irrigator when said irrigating brush accessory is attached thereto;

a first one-way valve accommodated within said lumen in close proximity to said fluid outlet for enabling said irrigation fluid to flow from said bulb through said flexible tube, said nozzle and said irrigation means so as to be dispensed therefrom upon compression of said bulb and for preventing contaminated oral fluids from flowing into said cavity of said bulb by way of said irrigation means, said nozzle, and said flexible tube upon decompression of the bulb; and a second one-way valve for preventing flow of air and/or any additional irrigation fluid from said bulb through said flexible tube, said nozzle and said irrigation means when the bulb is compressed and permitting flow of air into the bulb during decompression.

3. An oral irrigator fluid dispensing apparatus according to claim 2 wherein said channel means comprises a lumen within said stem.

4. An oral irrigator fluid dispensing apparatus according to claim 2 wherein said nozzle constitutes a single part.

5. An oral irrigator fluid dispensing apparatus according to claim 2 wherein said nozzle comprises several parts which may be permanently or releasably mounted together.

6. An oral irrigator fluid dispensing apparatus according to claim 2 wherein said bulb is made from rubber.

7. An oral irrigator fluid dispensing apparatus according to claim 2 wherein said bulb is made from silicon rubber.

8. An oral irrigator fluid dispensing apparatus according to claim 2 wherein said bulb is made from soft polyvinylchloride.

9. An oral irrigator fluid dispensing apparatus according to claim 2 wherein said nozzle is made from a rigid plastic material.

10. An oral irrigator fluid dispensing apparatus according to claim 2 wherein part of said tube extending into the bulb is spiral.

11. An oral irrigator fluid dispensing apparatus according to claim 2 wherein part of said tube extending into the bulb is essentially non-spiral.

12. An oral irrigator fluid dispensing apparatus according to claim 2 wherein said tube is made of a material selected from the group consisting of polyvinylchloride, soft plastic material, rubber, silicon rubber or latex.

13. An oral irrigator fluid dispensing apparatus according to claim 2 wherein said weight is made from metal.

14. An oral irrigator fluid dispensing apparatus according to claim 2 wherein said fluid outlet is equipped with suitable means for attaching the irrigation means thereto.

15. An oral irrigator fluid dispensing apparatus according to claim 2, wherein said bulb is formed from an elastic material.

16. An oral irrigator fluid dispensing apparatus according to claim 15, wherein said bulb is compressible.

17. An oral irrigator fluid dispensing apparatus according to claim 2, wherein said base portion of said nozzle is formed from a rigid material.

18. An oral irrigator fluid dispensing apparatus according to claim 2, wherein said tube includes a spiral portion which is located in said internal cavity of said bulb.

19. An oral irrigator fluid dispensing apparatus according to claim 2, wherein said tube has an essentially non-spiral shape.

20. An oral irrigator fluid dispensing apparatus according to claim 2, wherein said tube is formed from a relatively soft material.

21. An oral irrigator fluid dispensing apparatus according to claim 2, wherein said weight is formed from a material having a relatively high specific gravity.

22. An oral irrigator fluid dispensing apparatus according to claim 2, wherein said first one-way valve is located within said lumen of said nozzle.

23. An oral irrigator fluid dispensing apparatus according to claim 2, wherein said second one-way valve is coupled to an outside wall of said bulb.

24. An oral irrigator fluid dispensing apparatus according to claim 2, wherein said second one-way valve is coupled to said nozzle.

25. An oral irrigator fluid dispensing apparatus according to claim 2 wherein said weight is made from a material having a high specific gravity.

26. The oral irrigator fluid dispensing apparatus of claim 2 wherein said weight can be made of a heavy plastic material having a high specific gravity.

27. The oral irrigator fluid dispensing apparatus of claim 2 wherein said weight is made from glass.

28. An oral irrigator fluid dispensing apparatus comprising:

an elastic compressible bulb having an opening and an internal cavity for holding an irrigation fluid therein and wherein the irrigation fluid always settles to a low region of the internal cavity within the bulb in any spatial orientation of the bulb;

a weight;

a rigid nozzle having a base portion to which the bulb opening is attached, a lumen having a fluid outlet at an upper portion thereof, and a flexible, non-kinking tube, one end of said tube being coupled to a lower portion of said lumen and another fluid inlet end being attached to said weight and extending into said cavity of said bulb to provide for means for constantly maintaining said fluid inlet end of said tube in the irrigation fluid regardless of the spatial orientation of the bulb, with the tube being of a sufficient length and flexibility such that with the cooperation of the weight, the fluid inlet end of the tube is contained in said low area so as to enable the irrigation fluid to flow through the flexible tube to the nozzle regardless of the spatial orientation of said bulb;

irrigation means coupled to said fluid outlet of said lumen for dispensing said irrigation fluid therefrom by compressing said bulb and including an irrigating brush accessory having a stem comprising suitable bristles at a first end thereof and suitable channel means communicating between at least one brush fluid outlet located at or near said first end, and said lumen of said oral irrigator when said irrigating brush accessory is attached thereto;

a first one-way valve accommodated within said irrigation means for enabling said irrigation fluid to flow from said bulb through said flexible tube, said nozzle and said irrigation means so as to be dispensed therefrom upon compression of said bulb and for preventing contaminated oral fluids from flowing into said cavity of said bulb by way of said irrigation means, said nozzle, and said flexible tube upon decompression of the bulb; and a second one-way valve for preventing flow of air and/or any additional irrigation fluid from said bulb through said flexible tube, said nozzle and said irrigation means when the bulb is compressed and permitting flow of air into the bulb during decompression.

29. An oral irrigator fluid dispensing apparatus according to claim 28 wherein said channel means comprises a lumen within said stem.

* * * * *